United States Patent
Suzuki et al.

(10) Patent No.: US 9,829,461 B2
(45) Date of Patent: Nov. 28, 2017

(54) MEASURING DEVICE

(71) Applicant: HORIBA Advanced Techno, Co., Ltd., Kyoto-shi, Kyoto (JP)

(72) Inventors: Riichiro Suzuki, Kyoto (JP); Kentaro Inoue, Kyoto (JP)

(73) Assignee: HORIBA Advanced Techno, Co., Ltd., Kyoto-shi, Kyoto (JP)

( * ) Notice: Subject to any disclaimer, the term of this patent is extended or adjusted under 35 U.S.C. 154(b) by 50 days.

(21) Appl. No.: 14/648,238

(22) PCT Filed: Nov. 15, 2013

(86) PCT No.: PCT/JP2013/080937
§ 371 (c)(1),
(2) Date: May 28, 2015

(87) PCT Pub. No.: WO2014/084068
PCT Pub. Date: Jun. 5, 2014

(65) Prior Publication Data
US 2015/0308975 A1   Oct. 29, 2015

(30) Foreign Application Priority Data

Nov. 29, 2012  (JP) ................................ 2012-261612

(51) Int. Cl.
*G01N 27/404* (2006.01)
(52) U.S. Cl.
CPC .................. *G01N 27/404* (2013.01)
(58) Field of Classification Search
CPC ...... G01N 27/28; G01N 27/40; G01N 27/404; G01N 27/413; G01N 27/4045
See application file for complete search history.

(56) References Cited

U.S. PATENT DOCUMENTS

| 4,435,268 A | * | 3/1984 | Martin | ................. | G01N 27/404 204/408 |
| 5,690,808 A | * | 11/1997 | Akmal | ................. | G01N 27/404 204/412 |
| 6,024,853 A | * | 2/2000 | Kiesele | ................. | G01N 27/404 204/402 |

FOREIGN PATENT DOCUMENTS

| GB | 2013895 A | * | 8/1979 | .......... G01N 27/404 |
| JP | 53050892 A | | 5/1978 | |
| JP | 60200159 A | * | 10/1985 | |
| JP | 6157853 U | | 4/1986 | |
| JP | 62067443 A | * | 3/1987 | |
| JP | 04215897 A | | 8/1992 | |
| JP | 06194335 A | | 7/1994 | |
| JP | 06222038 A | | 8/1994 | |

OTHER PUBLICATIONS

Machine translation of JP 62-067443.*
(Continued)

*Primary Examiner* — Keith Hendricks
*Assistant Examiner* — Joshua Allen
(74) *Attorney, Agent, or Firm* — Alleman Hall Creasman & Tuttle LLP

(57) ABSTRACT

A measuring device comprises a guard electrode that is arranged around a cathode, reduces oxygen that is not from an oxygen permeable membrane, and inhibits the oxygen from reaching the cathode. The guard electrode is electrically connected to an anode through a resistor having a prescribed resistance.

4 Claims, 6 Drawing Sheets

(56) References Cited

OTHER PUBLICATIONS www.dictionary.com definition of Resin (screenshot).*
ISA Japanese Patent Office, International Search Report Issued in Application No. PCT/JP2013/080937, Jan. 28, 2014, WIPO, 4 pages.

* cited by examiner

MEASURING DEVICE

FIELD OF THE ART

This invention relates to a measuring device such as a dissolved oxygen analyzer that reduces or oxidizes an object substance such as oxygen or the like that enters from a measurement sample by permeating through a permeable member by the use of one of a pair of electrodes that are immersed in an electrolytic solution and that measures a concentration of the object substance in the measurement sample based on a value of an electric current that flows between the above-mentioned a pair of electrodes at a time when the object substance is reduced or oxidized.

BACKGROUND ART

A problem that is common to this kind of measuring devices such as the dissolved oxygen analyzer is consumption of an electrolytic solution. The electrolytic solution into which a pair of the electrodes (an anode and a cathode) are immersed is consumed because of an electrochemical reaction on the electrodes at a time of the measurement and eventually the measurement becomes impossible. As a result of this, it becomes necessary to exchange the electrolytic solution according to the use of the measuring device. If the measuring device is of a type wherein the electrolytic solution is unexchangeable, it is necessary to exchange the measuring device itself.

The patent document 1 describes, for example, a means to restrain consumption of the electrolyte solution as a measure to reduce a frequency of exchanging the electrolyte solution in a field of the dissolved oxygen analyzer. Concretely, a cathode and an anode are connected through a wiring cable at a time when the measuring device is used, and a resistor is arranged between the cathode and the anode at a time when the measuring device is not used. With this arrangement, the electric current due to the electrochemical reaction at a time when the measuring device is not used is reduced and the consumption of the electrolytic solution can be reduced.

Meanwhile, in accordance with the dissolved oxygen analyzer having the above-mentioned arrangement, in case that the oxygen concentration in the measurement sample is low, the oxygen that originally exists in the electrolytic solution reacts on the cathode and a surplus current flows at a time of an initial measurement. As a result of this, it is not possible to secure the measurement accuracy until the existing oxygen is completely reduced so that there is a problem that the responsiveness is aggravated.

Then, in order to improve the responsiveness in case that an oxygen concentration is low, a noise removing electrode as being a guard electrode is arranged to surround the cathode, and all of the oxygen contained in the electrolytic solution outside of the guard electrode is reduced on the guard electrode so that the oxygen that is not from the measuring sample does not reach the cathode.

However, with this arrangement, in case that the oxygen concentration is high, the reaction amount of the oxygen in the measuring sample reduced on the guard electrode increases so that there is a problem that the electrolytic solution is quickly consumed. Especially, in relation to an arrangement that the guard electrode surrounds the cathode, a contact area (a reacting area) of the guard electrode to the electrolytic solution becomes bigger than the contact area of the cathode. Then, when the reduced reaction occurs, the amount of the reduced oxygen on the guard electrode becomes more than the amount of the reduced oxygen on the cathode. As a result of this, the electrolytic solution is heavily consumed.

This problem is common to not only the dissolved oxygen analyzer but also a measuring device that reduces the object substance such as oxygen that enters from the measuring sample through a permeable member by the use of the cathode that is immersed in the electrolytic solution or that oxidizes the object substance by the use of the anode that is immersed in the electrolytic solution, and that measures a concentration of the object substance in the measuring sample based on an value of an electric current that flows between the anode and the cathode at a time of reduction or oxidization.

PRIOR ART DOCUMENTS

Patent Document

Patent document 1: Japanese Unexamined Patent Application Publication No. 60 -200159

DISCLOSURE OF THE INVENTION

Problems to be Solved by the Invention

The present claimed invention intends to solve all of the problems and a main object of this invention is to provide a measuring device that can measure a concentration of the object substance with high responsiveness in case that the concentration of the object substance in the measuring sample is low and that can reduce a consumed amount of the electrolytic solution.

Means to Solve the Problems

More specifically, a measuring device in accordance with this invention comprises a casing having a permeable member through which an object substance permeates into a measurement sample and a pair of electrodes, namely, a first electrode and a second electrode immersed in an electrolytic solution filled in the casing, and that measures the object substance in the measurement sample based on an electric current value that flows through the first electrode and the second electrode in case that the object substance in the measurement sample entering inside the casing through the permeable member is reduced or oxidized on the first electrode.

In addition, the measuring device further comprises a guard electrode that is arranged around the first electrode, that is connected to the second electrode or another electrode immersed in the electrolytic solution and that reduces or oxidizes the object substance contained in the electrolytic solution outside of the guard electrode so as to inhibit the object substance from reaching the first electrode, and is characterized by that the guard electrode is electrically connected to the second electrode or the above-mentioned another electrode through a resistor having a prescribed resistance.

In accordance with this measuring device, in case that the substance that the object substance is reduced is, for example, oxygen, chlorine, ozone, hydrogen peroxide or peracetic acid, it is necessary to set the first electrode as the cathode, and the second electrode as the anode. Meanwhile, in case that the substance that the object substance is oxidized is, for example, hydrogen, it is necessary to set the first electrode as the anode, and the second electrode as the cathode. In addition, it is necessary to select a material of the guard electrode suitably tailored to the first electrode.

In accordance with this arrangement, in case that the concentration of the object substance in the measurement sample is low and a subtle amount of the object substance in the electrolytic solution can be an impeding factor of a measurement responsiveness, the object substance in the electrolytic solution is reduced or oxidized on the guard electrode so as not to make the object substance reach the first electrode. As a result of this, the measurement accuracy can be secured without sacrificing the responsiveness. This is because that the object substance reduced on the guard electrode is a total of the object substance entering from the measurement sample through the permeable membrane and the object substance originally existing in the electrolytic solution, however the total amount is subtle so that the electric current flowing through the second electrode (or another electrode) and the guard electrode also becomes subtle, resulting in almost no voltage drop in the resistor. In addition, since the voltage in the guard electrode to the second electrode (or another electrode) is substantially kept with or without the resistor, the oxidization reaction or the reduction reaction of the object substance on the guard electrode, in other words, the guard action is carried out sufficiently.

Meanwhile, in case that the concentration of the object substance in the measurement sample is high to a degree wherein the guard electrode is unnecessary, the object substance from the measurement sample is reduced or oxidized on the guard electrode so that a considerable amount of the electric current attempts to flow through the second electrode (or another electrode) and the guard electrode, resulting in the voltage drop in the resistor due to the electric current. As a result of this, it is not possible to keep the voltage in the guard electrode so that the reduction reaction or the oxidization reaction of the object substance is restrained and the electric current is reduced.

As a result of this, the guard action drops and a part of the object substance in the electrolytic solution reaches the first electrode and is reduced or oxidized. However, since the concentration of the object substance in the measurement sample is high, even though a subtle amount of the object substance in the electrolytic solution is reduced or oxidized on the first electrode and its electric current is added to the electric current due to the object substance from the measurement sample, no substantial influence is not exerted on the measurement accuracy.

In addition, since the electrochemical reaction generated on the guard electrode and the second electrode (or another electrode) is restricted compared with a case of no resistor, it is possible to suppress unnecessary consumption of the electrolytic solution so that the life of the electrolytic solution can be elongated or an amount of the electrolytic solution can be reduced.

As a concrete embodiment of this invention can be represented is the measuring device, wherein the first electrode is in a pin shape and its distal end surface is arranged in close proximity to or in contact with the permeable member, and the guard electrode is in a cylindrical shape that surrounds a side peripheral surface of the first electrode and that is arranged to be separated from the first electrode, and its distal end surface is arranged in close proximity to or in contact with the permeable member.

In order to make the effect of this invention more conspicuous while avoiding unnecessary consumption of the electrolytic solution, it is preferable that the first electrode is so configured that the side peripheral surface is covered with a resin and only its distal end surface is exposed to the electrolytic solution, and the guard electrode is so configured that its inner side peripheral surface and its outer side peripheral surface are covered with a resin and only its distal end surface is exposed to the electrolytic solution.

In order to make it possible to adjust the guard action, it is preferable that the resistor is a variable resistor.

Effect of the Invention

As mentioned above, in accordance with this invention, in case that the concentration of the object substance in the measurement sample is low, since the guard electrode sufficiently exerts its function, it is possible to measure the concentration of the object substance with high responsiveness. In case that the concentration of the object substance is high, although the function as the guard electrode is lost, the responsiveness and the measurement accuracy accompanying this will not drop substantially because the guard electrode is not necessary in the first place. As a result of this, it is possible to conduct the measurement with high accuracy without sacrificing the responsiveness over a wide measurement range.

In addition, in case that the concentration of the object substance in the measurement sample is high or in case that the guard electrode is exposed to the object substance whose concentration is high while no measurement is conducted, since the reduction reaction or the oxidization reaction occurred in the guard electrode can be restrained by the resistor, it is possible to restrain useless consumption of the electrolytic solution and to elongate the life span of the electrolytic solution or to lessen the electrolytic solution. Especially, in manufacturing semiconductors, since continuous operation is often required, the frequency of exchanging the electrolytic solution is high so that the effect of this invention becomes conspicuous.

BEST MODES OF EMBODYING THE INVENTION

One embodiment of this invention will be explained with reference to drawings.

Figure 1:
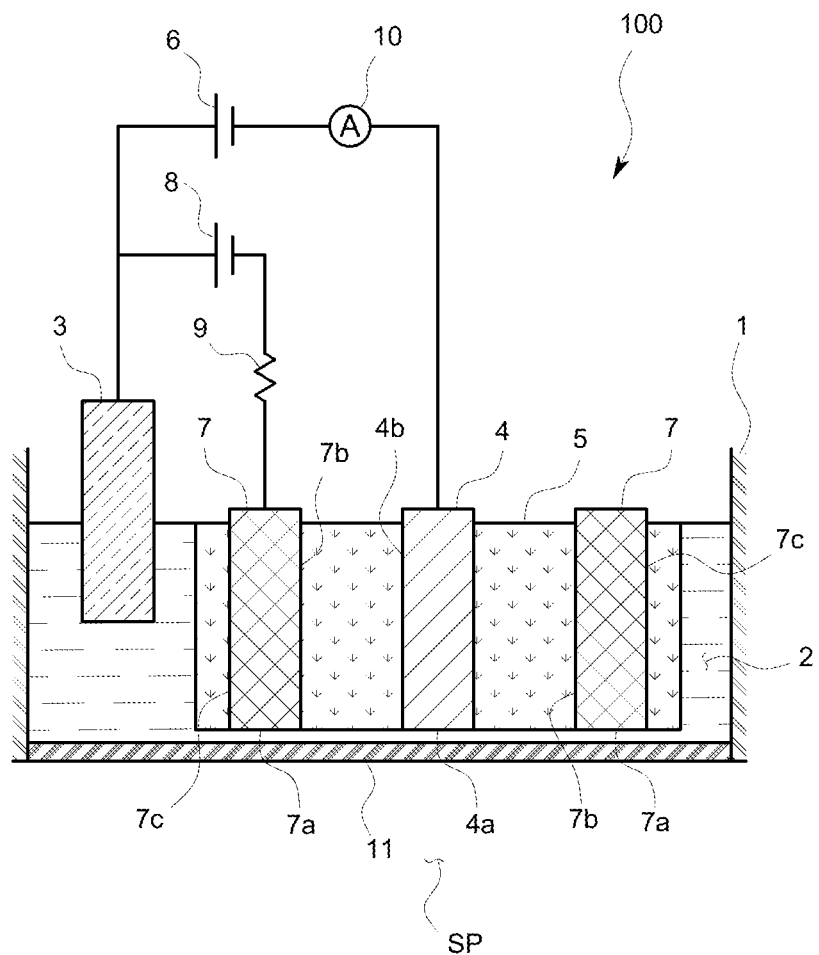
FIG. 1 is a longitudinal sectional pattern view showing an internal configuration of a dissolved oxygen analyzer in accordance with one embodiment of this invention.
Figure 2:
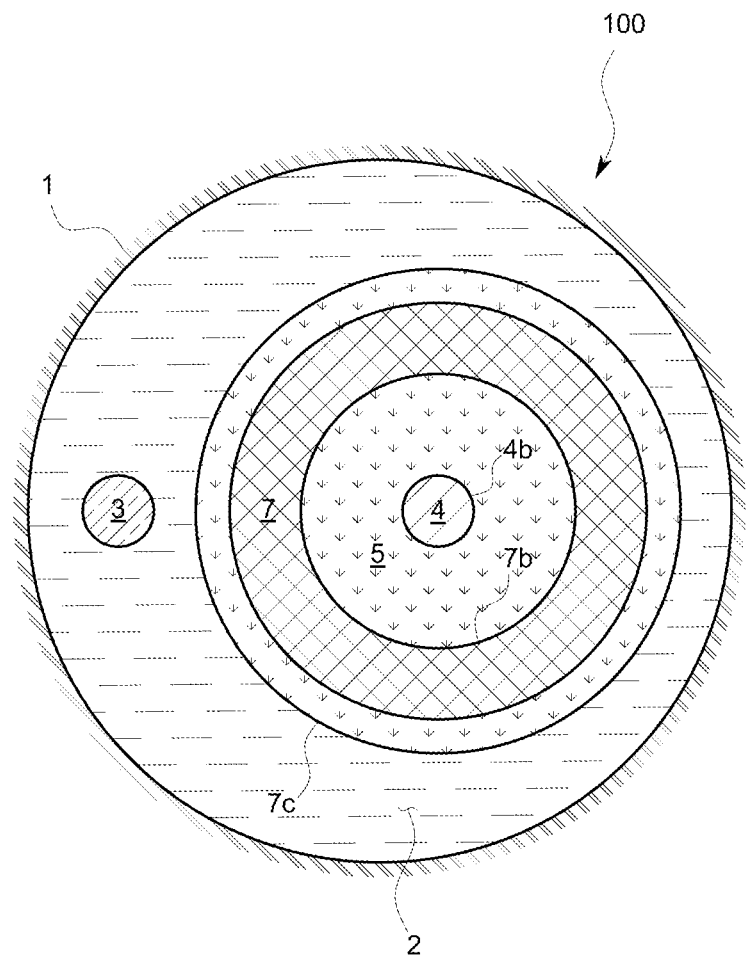
FIG. 2 is a transverse sectional pattern view showing the internal configuration of the dissolved oxygen analyzer in accordance with this embodiment.

A dissolved oxygen analyzer 100 as being a measuring device in accordance with this embodiment is to measure oxygen in a hydrofluoric acid solution flowing in a hydrofluoric acid line of, for example, a semiconductor manufacturing equipment, and as shown in FIG. 1 and FIG. 2, comprises a casing 1 provided with an oxygen permeable membrane 11 as being a permeable member at a distal end of the casing 1, a cathode 4 and an anode 3 as being a pair of electrodes, namely, a first electrode and a second electrode that are immersed into an electrolytic solution 2 in the casing 1. The dissolved oxygen analyzer 100 measures a concentration of oxygen in a measurement sample (SP) by reducing oxygen in the measurement sample (SP) entering inside of the dissolved oxygen analyzer 100 from the outside of the dissolved oxygen analyzer 100 through the oxygen permeable membrane 11 by the use of the cathode 4 as being the first electrode and by measuring an electric current flowing through the cathode 4 and the anode 3 as being the second electrode by the use of an ammeter 10 at a time when the oxygen is reduced.

FIG. 1 is a longitudinal sectional pattern view showing an internal configuration and an electric circuit of the dissolved oxygen analyzer 100, and FIG. 2 is a transverse sectional pattern view showing the internal configuration of the dissolved oxygen analyzer 100.

Each part will be described in detail.

The casing 1 is in a tubular shape whose distal end part is formed by the oxygen permeable membrane 11. Inside of the casing 1 filled is, for example, a KCl solution as the electrolytic solution 2.

The anode 3 is a silver electrode whose shape is, for example, a pin shape, and is immersed in the electrolytic solution 2 in a peripheral edge part of the casing 1.

The cathode 4 is a gold electrode whose shape is, for example, a pin shape, and is electrically connected to the anode 3. A distal end surface 4a of the cathode 4 is arranged in proximity to an inner surface of the oxygen permeable membrane 11 and a side peripheral surface 4b of the cathode 4 in the electrolytic solution 2 is covered with a resin 5 so as to make only the distal end surface 4a touch the electrolytic solution 2 to generate the reductive reaction of the oxygen.

In this embodiment, the electrochemical reduction of the oxygen on the cathode 4 is conducted by the controlled potential electrolysis method (the polarographic method) by the use of a first constant voltage power supply 6, and electrical potential of the cathode 4 is kept at, for example, −0.6v that is lower than the electrical potential of the anode 3. Its pattern electrical circuit view is shown in FIG. 1. Practically the electric circuit is embodied by the use of an amplifier or a buffer, however its detail is omitted to explain. In addition, the electrochemical reduction of the oxygen on the cathode 4 may be conducted by the Galvanic cell type without using a constant voltage power supply. In this case, the anode may use, for example, a lead electrode, and the cathode may use, for example, a silver electrode.

In this embodiment, a cylindrical guard electrode 7 is arranged to be separately from the cathode 4 and to surround the side peripheral surface 4b of the cathode 4, and similar to the cathode 4, a distal end surface 7a of the guard electrode 7 is arranged to be in proximity to the inner surface of the oxygen permeable membrane 11. In addition, an inner side peripheral surface 7b and an outer side peripheral surface 7c of the guard electrode 7 are covered with a resin 5 and only the distal end surface 7a is in contact with the electrolytic solution 2. Especially, the resin of the inside of the guard electrode 7 reaches the cathode 4 and is filled into a space between the cathode side peripheral surface 4b and the guard electrode inside peripheral surface 7b without any void. The resin covering the outer side peripheral surface 7c of the guard electrode 7 may be omitted.

The guard electrode 7 in this embodiment is, for example, a gold electrode that is electrically connected to the anode 3. Similar to the cathode 4, the guard electrode 7 electrochemically reduces the oxygen by the distal end surface 7a. The electrochemical reduction of the oxygen on the guard electrode 7 is conducted by the controlled potential electrolysis method (the polarographic method) by the use of a second constant voltage power supply 8 that is different from the first constant voltage power supply 6, and electrical potential of the guard electrode 7 is kept at, for example, −0.6v that is lower than the electrical potential of the anode 3. Similar to the cathode 4, the electrochemical reduction of the oxygen on the guard electrode 7 may be conducted by the Galvanic cell type without using a constant voltage power supply. In this case, the anode may use, for example, a lead electrode, and the guard electrode may use, for example, a silver electrode.

Figure 3:
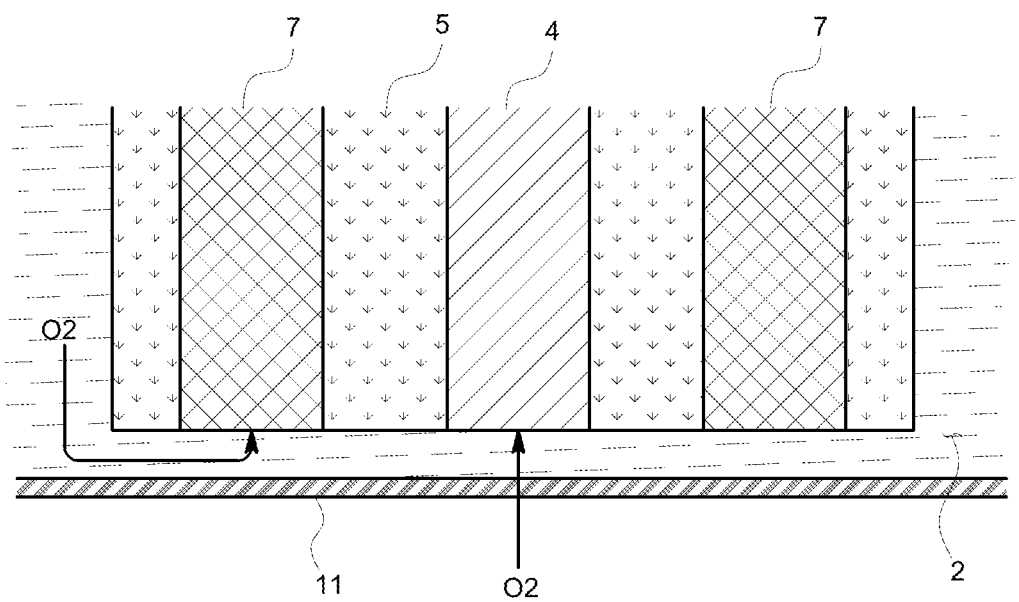
FIG. 3 is an enlarged partial longitudinal sectional pattern view showing the internal configuration of the dissolved oxygen analyzer in accordance with this embodiment.

It is a matter of course that the oxygen that permeates the oxygen permeable membrane 11 is reduced by the guard electrode 7. However, as shown in FIG. 3, since the oxygen that originally exists outside of the guard electrode 7 in the electrolytic solution 2 is also reduced, the guard electrode 7 acts a guard action of inhibiting the oxygen from being reduced by the cathode 4. Since only the oxygen from the measurement sample (SP) is reduced on the cathode 4 due to this guard action, it becomes possible to conduct a high responsiveness measurement without waiting the time period while the originally existing oxygen in the electrolytic solution 2 is completely reduced on the cathode 4.

In this embodiment, as shown in FIG. 1, the guard electrode 7 is electrically connected to the anode 3 through a resistor 9 having a prescribed resistance. Although the resistance depends on the measurement sample (SP), the resistance is preferably about 10 kΩ~100 kΩ and may be about 10 kΩ~500 kΩ.

In accordance with this arrangement, in case that the concentration of the oxygen in the measurement sample (SP) is low and a subtle amount of the oxygen in the electrolytic solution 2 can be an impeding factor of a measurement with high accuracy, it is possible for the guard electrode 7 to reduce the oxygen in the electrolytic solution 2 so as to hinder the oxygen from reaching the cathode 4. As a result of this, the measurement accuracy can be secured. This is because that the oxygen reduced in the guard electrode 7 is a total of the oxygen entering from the measurement sample (SP) through the oxygen permeable membrane 11 and the oxygen originally existing in the electrolytic solution 2, however the total amount is subtle so that the electric current flowing through the anode 3 and the guard electrode 7 also becomes subtle. As a result of this, almost no voltage drops in the resistor 9. In other words, since the voltage of the guard electrode 7 to the anode 3 is substantially the same with or without the resistor 9, the oxygen reducing action is sufficiently conducted on the guard electrode 7 so that the guard action is carried out normally. As a result of this, the measurement accuracy can be secured without sacrificing the responsiveness.

Meanwhile, in case that the oxygen concentration in the measurement sample (SP) is high to a degree wherein the guard electrode 7 is unnecessary, the oxygen from the measurement sample (SP) is reduced on the guard electrode 7 so that a considerable amount of the electric current attempts to flow through the anode 3 and the guard electrode 7. Then, the voltage drops in the resistor 9 because of this electric current so that it becomes difficult to keep the voltage in the guard electrode 7 to the anode 3. As a result of this, the oxygen reducing action is restrained and the electric current is reduced.

As a result of this, the guard action decreases and a part of the oxygen in the electrolytic solution 2 reaches the cathode 4 and is reduced on the cathode 4. However, since the oxygen concentration in the measurement sample (SP) is high, even though a subtle amount of the oxygen in the electrolytic solution 2 is reduced on the cathode 4 and its electric current is added to the electric current due to the oxygen from the measurement sample (SP), no substantial influence is not exerted on the measurement accuracy or the responsiveness.

Furthermore, since the electrochemical reaction generated on the guard electrode 7 and the anode 3 is restricted compared with a case of no resistor 9, it is possible to suppress an unnecessary consumption of the electrolytic solution 2 and to elongate the life of the electrolytic solution 2.

The present claimed invention is not limited to the above-mentioned embodiment. For example, a substance or a material of the electrolytic solution 2, the anode 3, the cathode 4 and the guard electrode 7 may be variously modified depending on the measurement sample (SP). In accordance with this modification, a voltage of the constant voltage power supply 6 may be different from that of the above-mentioned embodiment. The guard electrode 7 and the cathode 4 may not necessarily be of the same material.

Figure 4:
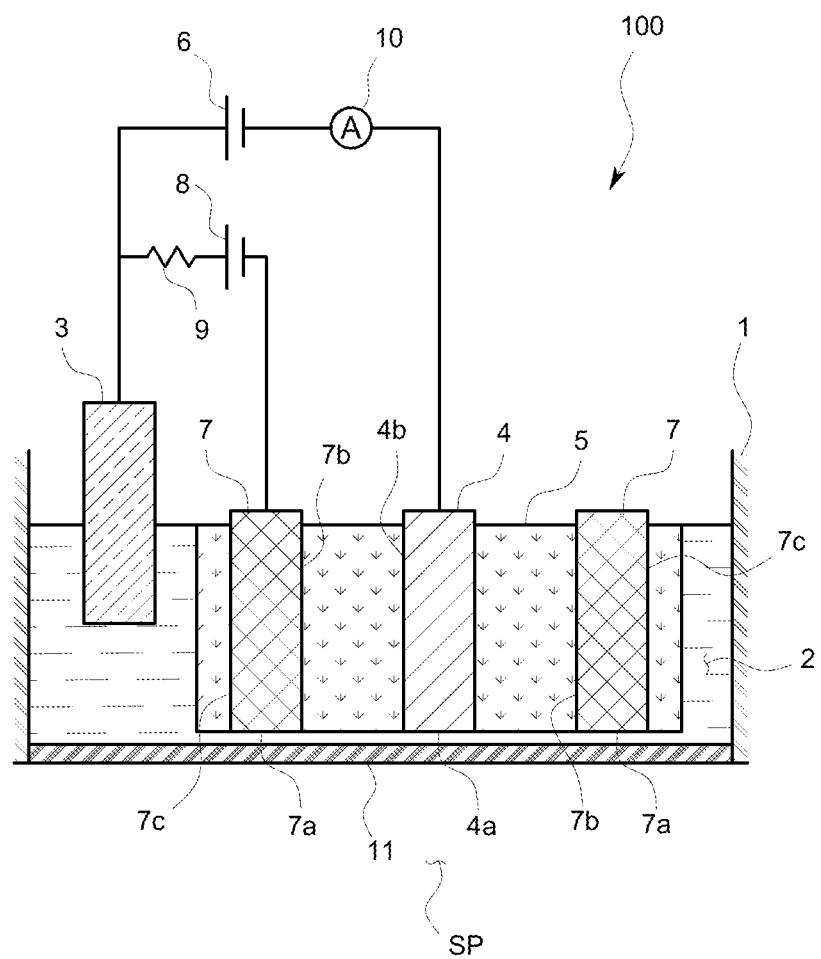
FIG. 4 is a longitudinal sectional pattern view of an internal configuration of a dissolved oxygen analyzer in accordance with another embodiment of this invention.
Figure 5:
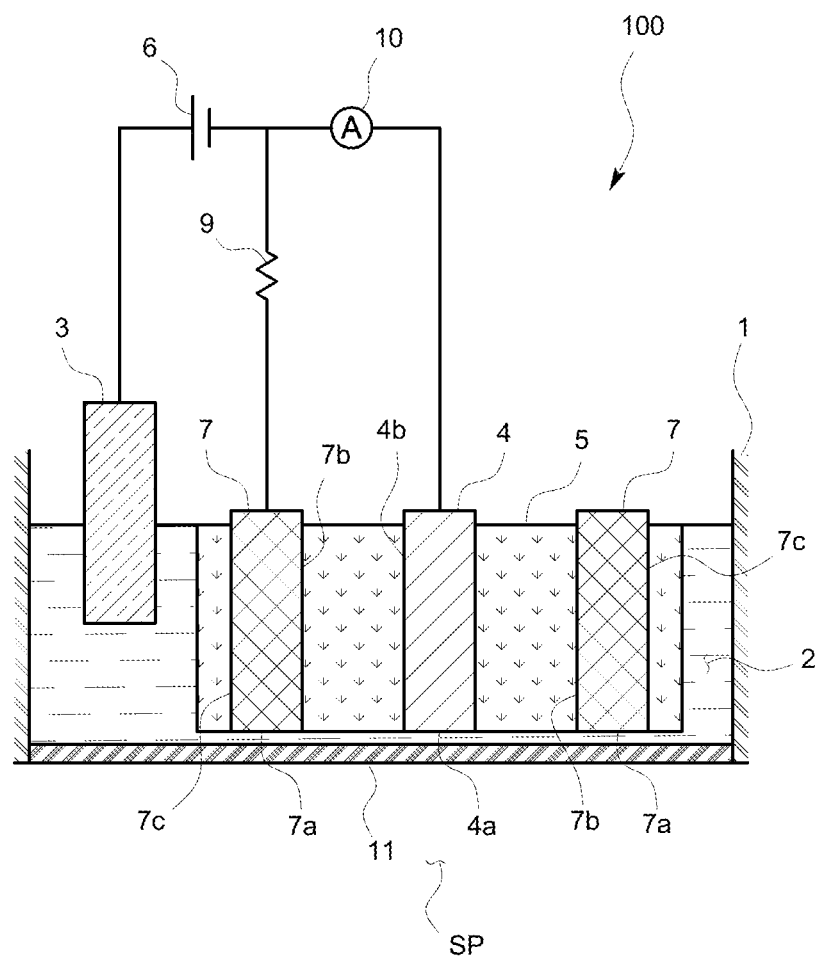
FIG. 5 is a longitudinal sectional pattern view of an internal configuration of a dissolved oxygen analyzer in accordance with a further different embodiment of this invention.

In addition, the resistor 9 is arranged between the second constant voltage power supply 8 and the guard electrode 7 in FIG. 1, however, the resistor 9 may be arranged between the second constant voltage power supply 8 and the anode 3 as shown in FIG. 4. The constant voltage power supply may be a single constant voltage power supply 6, and the resistor 9 may be arranged on a branch wiring to the guard electrode 7 as shown in FIG. 5.

Figure 6:
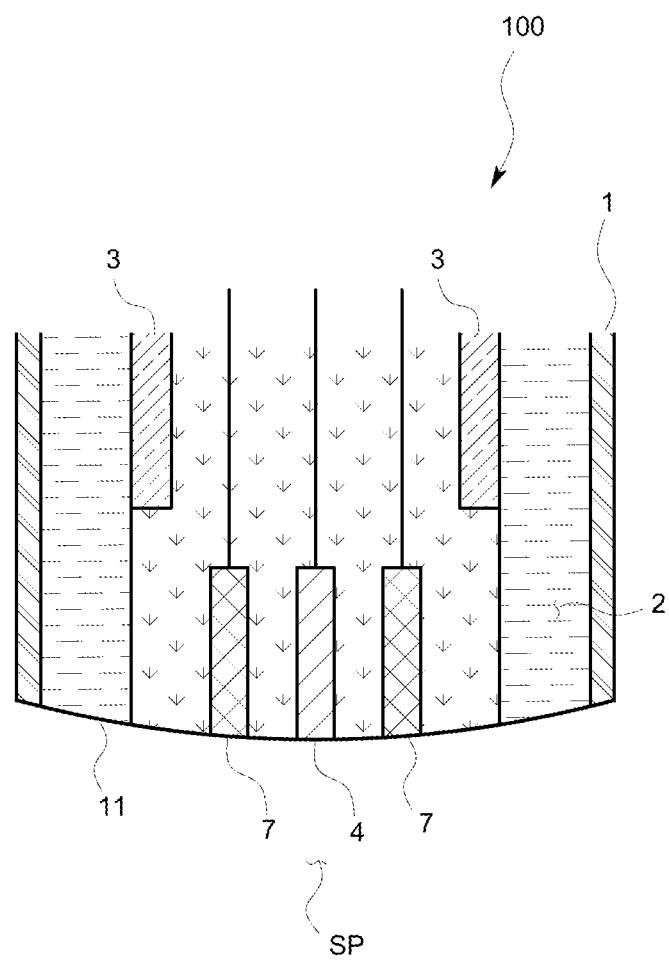
FIG. 6 is a longitudinal sectional pattern view of an internal configuration of a dissolved oxygen analyzer in accordance with a further different embodiment of this invention.

Furthermore, a physical arrangement of the anode, the cathode and the oxygen permeable membrane may be variously modified, and the arrangement may be, for example, as shown in FIG. 6. In FIG. 6, the cathode 4 projects from a distal end of a peripheral wall of the casing 1 and the oxygen permeable membrane 11 is arranged in a stretched state so that a center of the oxygen permeable membrane 11 protrudes. With this arrangement, it is possible to stretch the oxygen permeable membrane 11 without slack. In addition, although the distal end surface of the cathode 4, the distal end surface of the guard electrode 7 and the distal end surface of the resin 5 make in contact with the oxygen permeable membrane 11, since the electrolytic solution 2 infiltrates into the gap therebetween and reaches the cathode 4 or the guard electrode 7, there is no chance that the electrochemical reaction is disturbed. Furthermore, in FIG. 6, the anode 3 is made to be in a cylindrical shape and integrally mounted on the outside peripheral surface of the resin 5 and the electrolytic solution 2 is filled into outside of the anode 3.

In addition, an anode (corresponds to the second electrode in claims) for the guard electrode immersed into the electrolytic solution may be provided in addition to the anode for the cathode.

The guard electrode may not be in a perfect cylindrical shape as far as it locates around the cathode. The guard electrode may have a void or may be of a configuration wherein a plurality of pins are intermittently arranged.

In addition, the present claimed invention is not limited to the dissolved oxygen analyzer, and it is possible for the present claimed invention to measure a concentration of various substances. For example, chlorine, ozone, hydrogen peroxide and hydrogen. If it is necessary to provide the oxidization reaction such as hydrogen, it is necessary to exchange the anode and the cathode in the above-mentioned embodiment. In addition, it is necessary to use a member that permeates each substance as the permeable membrane or the permeable member. Furthermore, the measurement sample is not limited to a liquid, and may be a gas.

In addition, the present claimed invention is not limited to the above-mentioned embodiment and may be variously modified without departing from a spirit of the invention.

EXPLANATION OF CODES

100 . . . dissolved oxygen analyzer (measuring device)
SP . . . measurement sample
11 . . . oxygen permeable membrane (permeable member)
1 . . . casing
2 . . . electrolytic solution
3 . . . anode (second electrode)
4 . . . cathode (first electrode)
7 . . . guard electrode
9 . . . resistor

The invention claimed is:

1. A measuring device that comprises a casing having a permeable member through which an object substance permeates into a measurement sample and a pair of electrodes, namely, a first electrode and a second electrode immersed in an electrolytic solution filled in the casing, and that measures the object substance in the measurement sample based on a value of an electric current that flows through the first electrode and the second electrode in case that the object substance in the measurement sample entering inside the casing through the permeable member is reduced or oxidized on the first electrode, further comprising
   a guard electrode that is arranged around the first electrode, and that is electrically connected to the second electrode or a third electrode immersed in the electrolytic solution, and that reduces or oxidizes the object substance contained in the electrolytic solution outside of the guard electrode so as to inhibit the object substance from reaching the first electrode, and
   a resistor having a prescribed resistance that is arranged on an electrical connection pathway between the guard electrode and the second electrode or between the guard electrode and the third electrode, thereby flowing current from the guard electrode through the resistor to the second electrode, or flowing current from the guard electrode through the resistor to the third electrode.

2. The measuring device described in claim 1, wherein the first electrode is in a pin shape and its distal end surface is arranged to be substantially in contact with the permeable member, and
   the guard electrode is in a cylindrical shape that surrounds a side peripheral surface of the first electrode and that is arranged to be separated from the first electrode, and its distal end surface is arranged to be substantially in contact with the permeable member.

3. The measuring device described in claim 2, wherein the first electrode is so configured that the side peripheral surface is covered with a resin and only its distal end surface is exposed to the electrolytic solution, and
   the guard electrode is so configured that its inner side peripheral surface and its outer side peripheral surface are covered with a resin and only its distal end surface is exposed to the electrolytic solution.

4. The measuring device described in claim 1, wherein the resistor is a variable resistor.

\* \* \* \* \*